US00PP27237P2

(12) United States Plant Patent
Klemm et al.

(10) Patent No.: US PP27,237 P2
(45) Date of Patent: Oct. 4, 2016

(54) ***PETUNIA* PLANT NAMED 'KLEPH15313'**

(50) Latin Name: *Petunia hybrida*
Varietal Denomination: KLEPH15313

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/545,759

(22) Filed: Jun. 15, 2015

(51) Int. Cl.
*A01H 5/02* (2006.01)

(52) U.S. Cl.
USPC ..... Plt./356.1

(58) Field of Classification Search
USPC ..... Plt./356.1, 356.2
CPC ..... A01H 5/02
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

A new *Petunia* plant particularly distinguished by blue flowers with white dots and a mounding/semi-trailing habit, is disclosed.

1 Drawing Sheet

Genus and species: *Petunia hybrida.*
Variety denomination: 'KLEPH15313'.

BACKGROUND OF THE NEW PLANT

The present invention comprises a new and distinct variety of *Petunia*, botanically known as *Petunia hybrida*, and hereinafter referred to by the variety name 'KLEPH15313'. 'KLEPH15313' originated from a cross-pollination conducted in July 2012 in Latina, Italy between the proprietary female *Petunia* variety 'PH-2012-3528' (unpatented) and the male *Petunia* variety 'Duesurmar' (U.S. Plant Pat. No. 21,673).

The seeds from the cross were sown and plants were grown in a greenhouse for evaluation, where an individual plant designated 'KLEPH15313' was selected from the group of plants in April 2013 in Latina, Italy. In May 2013, 'KLEPH15313' was first vegetatively propagated by terminal tip cuttings. 'KLEPH15313' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany and Latina, Italy.

1. Blue flowers with white dots; and
2. A mounding and semi-trailing habit.

CROSS-REFERENCE TO RELATED APPLICATIONS

Plant Breeders Rights for 'KLEPH 15313' were filed in Canada on Apr. 2, 2015, Application No. 15-8584. 'KLEPH15313' has not been sold or made publicly available more than one year prior to the filing date of this subject application.

DESCRIPTION OF THE PHOTOGRAPH

This new *Petunia* plant is illustrated by the accompanying photograph of a plant grown in a plastic greenhouse in Stuttgart, Germany. The photograph was taken in July 2014 and shows the foliage and flowers of a 4-month-old plant grown in a pot. The colors shown are as true as can be reasonably obtained by conventional photographic procedures.

DESCRIPTION OF THE NEW VARIETY

The following detailed descriptions set forth the distinctive characteristics of 'KLEPH15313'. The data which define these characteristics were collected from asexual reproductions carried out in Latina, Italy. Data was collected on plants grown 12-weeks from cultivation from potting in a plastic greenhouse in Latina, Italy in February 2015. Color references are to The R.H.S. Colour Chart of The Royal Horticultural Society of London (R.H.S.), 5$^{th}$ edition (2007).

Classification:
- *Family.*—Solanaceae.
- *Botanical.*—*Petunia hybrida.*
- *Common.*—*Petunia.*
- *Designation.*—'KLEPH15313'.

Parentage:
- *Female parent.*—The proprietary female *Petunia* variety 'PH-2012-3528' (unpatented).
- *Male parent.*—The male *Petunia* variety 'Duesurmar' (U.S. Plant Pat. No. 21,673).

Plant:
- *Vigor.*—Medium.
- *Habit.*—Mounding/semi-trailing.
- *Height (from top of soil).*—About 7.0 cm.
- *Width (horizontal plant diameter).*—About 16.0 cm.
- *Propagation.*—Terminal tip cuttings and tissue culture.
- *Time to produce a finished flowering plant.*—About 13 weeks in the winter under short day conditions, and 9 weeks in the spring.

*Time to initiate and develop roots.*—2 to 3 weeks.

*Root description.*—Moderate density, moderate branching, white roots.

Stems:

*Average number (basal).*—About 12.

*Length of basal branches (from the base of the stem to the tip).*—9.0 cm.

*Internode length.*—0.5 cm.

*Diameter of branches (from midpoint).*—0.4 cm.

*Stem color.*—RHS 145C.

*Anthocyanin.*—Absent.

*Texture.*—Tomentose.

Leaves:

*Arrangement.*—Alternate.

*Length.*—8.5 cm.

*Width.*—2.8 cm.

*Shape.*—Elliptic/spatulate.

*Apex.*—Acute.

*Base.*—Attenuate.

*Margin.*—Entire.

*Immature leaf color.*—Upper surface: RHS 146B. Lower surface: RHS 146C.

*Mature leaf color.*—Upper surface: RHS 137A. Lower surface: RHS 147B.

*Texture (both upper and lower surfaces).*—Tomentose.

*Venation pattern.*—Arcuate.

*Venation color.*—Upper surface: RHS 137A. Lower surface: RHS 148C.

*Petioles.*—Length: 2.0 cm. Diameter: 0.4 cm. Color: RHS 145C. Texture: Tomentose.

Flower buds:

*Shape.*—Irregular oblong.

*Length.*—3.5 cm to 4.5 cm.

*Diameter.*—0.7 cm.

*Color at tight bud.*—RHS N77B, RHS90B and RHS 145D.

*Texture.*—Slightly pubescent.

Inflorescence:

*Blooming habit (flowering season).*—Permanent flowering during summer time.

*Inflorescence type.*—Cymose.

*Number of flowers per node.*—1.

*Lastingness of individual blooms on the plant.*—7 to 10 days.

*Fragrance.*—Absent.

*Flowers.*—Arrangement: Composed of 5 petals fused at the base. Diameter (flower face): 6.0 cm. Depth (total length of flower): 5.8 cm. Throat/Funnel: Length: 3.0 cm. Diameter (at opening): 1.3 cm. Texture (both inner and outer surfaces): Smooth, glabrous. Petals: Color of petals, mature flower (fully opened): Upper surface: RHS 86B and RHS NN155D. Lower surface: RHS 86D and RHS NN155D. Apex: Mucronate. Base: Fused. Shape: Base fused in a funnel. Margin: Entire. Strength of waviness: Weak. Degree of lobation: Medium-weak. Calyx arrangement: Actinomorphic, composed of 5 sepals. Sepals: Color: Upper surface: RHS N137D. Lower surface: RHS 137C. Length: 0.8 cm. Width: 0.4 cm. Shape: Narrowly oblong. Apex: Acute. Base: Attenuate. Margin: Entire. Texture (both upper and lower surfaces): Pubescent.

*Pedicels.*—Color: RHS 144A. Length: 0.5 cm. Diameter: 0.15 cm. Texture: Pubescent.

Reproductive organs:

*Stamens.*—Quantity: 5. Shape: Needle with elliptic head. Filament: Length: 1.7 cm to 2.0 cm. Diameter: 0.01 cm. Color: RHS N188C. Anther: Shape: Elliptic. Color: RHS 188B. Length: 0.2 cm. Diameter: 0.15 cm. Pollen: Color: RHS 188A. Amount: Sparse.

*Pistils.*—Quantity per flower: 1. Length: 2.5 cm. Stigma color: RHS N138A. Style color: RHS 193A and RHS 83B.

Fruit and seed set: No fruit and seed set observed.

Disease and pest/insect resistance: No disease and pest/insect resistance observed.

COMPARISON WITH PARENTAL LINES AND KNOWN VARIETY

'KLEPH15313' is a distinct variety of *Petunia* and is distinguished from its parents as described in Table 1.

TABLE 1

Comparison with Parental Lines

| Characteristic | 'KLEPH15313' | Female Parent 'PH-2012-3528' | Male Parent 'Duesurmar' |
|---|---|---|---|
| Flower color | Blue with white dots | Blue with unstable white dots and portions | Blue |

'KLEPH15313' is a distinct variety of *Petunia* and differences between 'KLEPH15313' and the commercial variety 'Duesurmar' are described in Table 2.

TABLE 2

Comparison with Similar Variety

| Characteristic | 'KLEPH15313' | 'Duesurmar' |
|---|---|---|
| Flower color | Blue with white dots | Blue |

We claim:

1. A new and distinct variety of *Petunia* plant designated 'KLEPH15313' as illustrated and described herein.

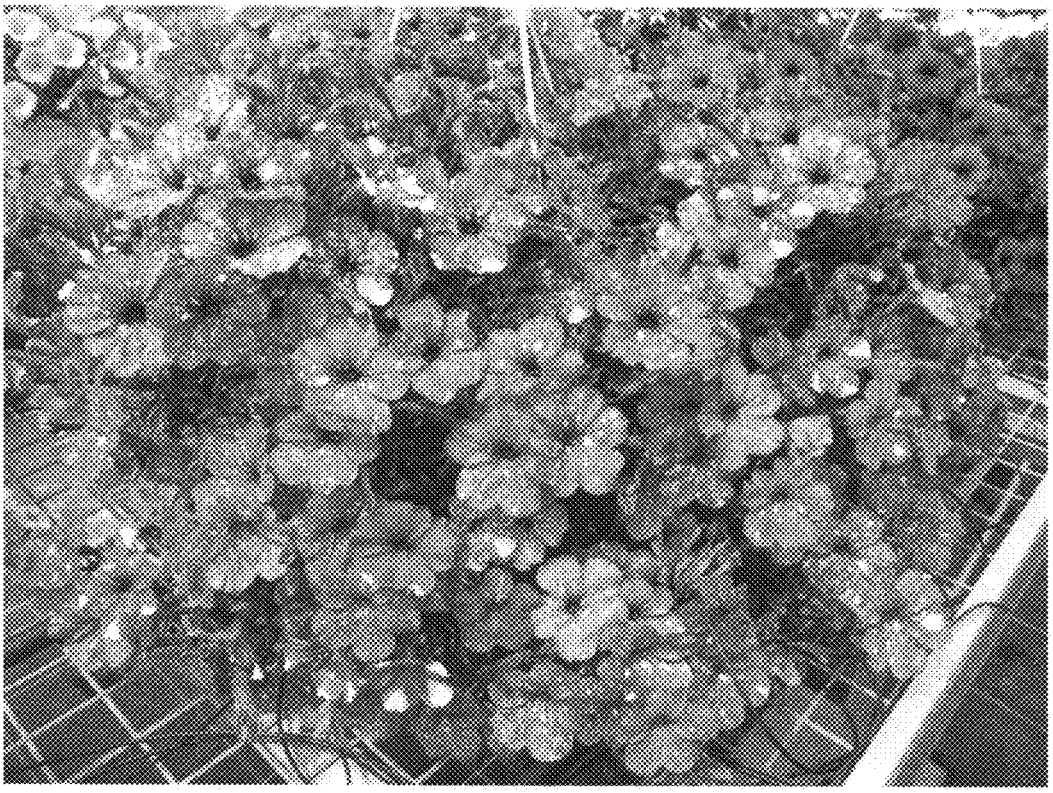

* * * * *